(12) United States Patent
Briand et al.

(10) Patent No.: US 11,191,704 B2
(45) Date of Patent: Dec. 7, 2021

(54) COMPOSITIONS AND METHODS FOR CONTROLLED MOISTURIZING AND RELEASE OF ACTIVE INGREDIENTS

(71) Applicant: AMANTIN EXPERTS, Paris (FR)

(72) Inventors: Elisabeth Briand, Gentilly (FR); Jean-Baptiste Dumas Milne Edwards, Paris (FR); Jacques Delort, Paris (FR)

(73) Assignee: AMANTIN EXPERTS, Paris (FR)

( * ) Notice: Subject to any disclaimer, the term of this patent is extended or adjusted under 35 U.S.C. 154(b) by 0 days.

(21) Appl. No.: 15/505,028

(22) PCT Filed: Aug. 20, 2014

(86) PCT No.: PCT/EP2014/067764
§ 371 (c)(1),
(2) Date: Feb. 17, 2017

(87) PCT Pub. No.: WO2016/026527
PCT Pub. Date: Feb. 25, 2016

(65) Prior Publication Data
US 2017/0246090 A1    Aug. 31, 2017

(51) Int. Cl.
| | | |
|---|---|---|
| *A61K 8/02* | (2006.01) | |
| *A61K 8/34* | (2006.01) | |
| *A61K 8/37* | (2006.01) | |
| *A61K 8/92* | (2006.01) | |
| *A61Q 19/00* | (2006.01) | |
| *A61K 8/49* | (2006.01) | |
| *A61K 8/67* | (2006.01) | |
| *A61K 9/00* | (2006.01) | |
| *A61K 31/122* | (2006.01) | |
| *A61K 47/10* | (2017.01) | |
| *A61K 47/14* | (2017.01) | |
| *A61K 47/44* | (2017.01) | |

(52) U.S. Cl.
CPC ............ *A61K 8/0295* (2013.01); *A61K 8/345* (2013.01); *A61K 8/375* (2013.01); *A61K 8/4973* (2013.01); *A61K 8/676* (2013.01); *A61K 8/922* (2013.01); *A61K 9/0014* (2013.01); *A61K 31/122* (2013.01); *A61K 47/10* (2013.01); *A61K 47/14* (2013.01); *A61K 47/44* (2013.01); *A61Q 19/00* (2013.01)

(58) Field of Classification Search
CPC .... A61K 8/0295; A61K 8/4973; A61K 8/676; A61K 9/0014; A61K 31/122; A61K 47/10; A61K 47/14; A61K 47/44; A61K 8/345; A61K 8/375; A61K 8/922; A61Q 19/00

See application file for complete search history.

(56) References Cited

U.S. PATENT DOCUMENTS

| | | | | |
|---|---|---|---|---|
| 4,203,969 | A * | 5/1980 | Yarrow | .................. A61K 8/347 514/732 |
| 4,695,452 | A * | 9/1987 | Gannis | .................. A61K 8/0229 424/59 |
| 2003/0219465 | A1 | 11/2003 | Gidwani et al. | |
| 2005/0238677 | A1 | 10/2005 | Mercier et al. | |
| 2009/0252773 | A1 | 10/2009 | Yoneda et al. | |
| 2009/0269394 | A1 * | 10/2009 | Baker, Jr. | ............. A61K 9/0014 424/447 |
| 2014/0274982 | A1 * | 9/2014 | Bakan | .................... A61K 31/58 514/174 |

FOREIGN PATENT DOCUMENTS

| | | | |
|---|---|---|---|
| FR | 2 685 202 | A1 | 6/1993 |
| WO | 00/51549 | A1 | 9/2000 |
| WO | 01/34111 | A1 | 5/2001 |
| WO | 2007/060177 | A1 | 5/2007 |

OTHER PUBLICATIONS

S.K. Raychaudhuri et al. / Autoimmunity Reviews 13 (2014) 490-495.*
https://www.livestrong.com/article/192009-skin-benefits-of-beeswax/, printed from web Dec. 7, 2018 (Year: 2018).*
Goddeeris, C., et al., "Lyotropic, Liquid Crystalline Nanostructures of Aqueous Dilutions of SMEDDS Revealed by Small-Angle X-Ray Scattering: Impact on Solubility and Drug Release," European Journal of Pharmaceutical Sciences 40(2): 110-117, May 2010.
International Search Report dated May 15, 2015, issued in corresponding International Application No. PCT/EP2014/067764, filed Aug. 20, 2014, 3 pages.

* cited by examiner

*Primary Examiner* — James W Rogers
(74) *Attorney, Agent, or Firm* — Christensen O'Connor Johnson Kindness PLLC

(57) ABSTRACT

The subject matter of the present invention is a cosmetic or pharmaceutical composition for controlled moisturizing and release of active molecule(s), comprising at least one emulsifier having an enzyme cleavable bound, at least one emollient, at least one polar solvent, and water, forming together a macroscopically homogenous liquid crystals emulsion. In some embodiments of the invention, the composition also includes at least one ingredient having a cosmetic or pharmaceutical activity.

21 Claims, 2 Drawing Sheets

Figure 1:
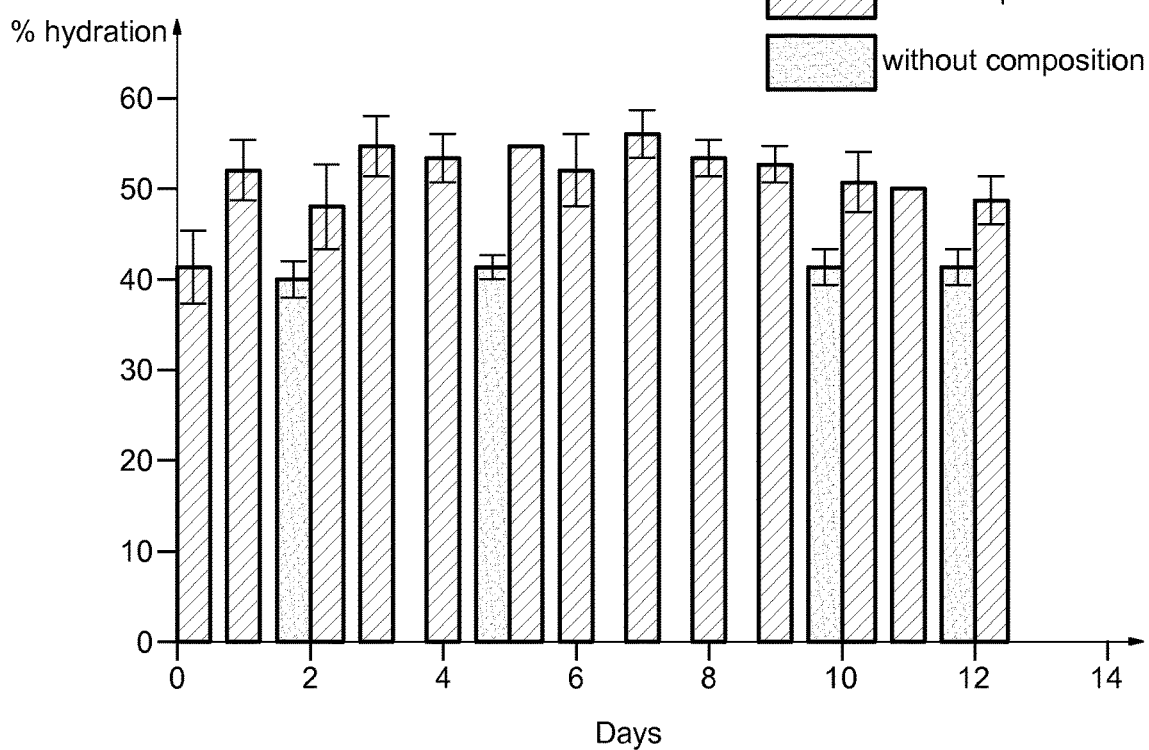

COMPOSITIONS AND METHODS FOR CONTROLLED MOISTURIZING AND RELEASE OF ACTIVE INGREDIENTS

The subject matter of the present invention is a cosmetic or pharmaceutical composition for controlled moisturizing and release of active molecule(s), comprising at least one emulsifier having an enzyme cleavable bound, at least one emollient, at least one polar solvent, and water, forming together a macroscopically homogenous liquid crystals emulsion. In some embodiments of the invention, the composition also includes at least one ingredient having a cosmetic or pharmaceutical activity.

The subject of the invention is also a method of cosmetically or pharmaceutically treating the skin or an internal tissue or organ, comprising applying the composition of the invention. Another subject of the invention is the use of this composition as a medicament.

Topical application of skincare products has proven to be an efficient way to maintain and restore healthy skin. To achieve this, it is essential to both moisturize skin—which involves bringing to skin an emollient, such as oil, to supple skin and an humectant, such as glycerin, which attracts water to the layers of the epidermis—and efficiently bring active ingredients having a bioactivity, which help to restore healthy skin conditions. Ideally, both the moisturizing and other active ingredients have to be released in a controlled way, to avoid their burst release, so as to reduce the need for applications. In addition, controlled release of the active ingredient(s) to the sites where they are most needed would allow minimizing side effects on healthy skin or tissue, thereby increasing the value of the products for patients and consumers. Moreover, most of these ingredients are sensitive molecules that should be protected toward oxidation when in pharmaceutical or cosmetic compositions.

An ideal formulation for a product designed for skincare or for delivery of active ingredients through skin should have the following properties to be able to ensure these functions: i) it should be acceptable for topical use, in particular it should provide a nice feel during application and should not give a tacky feel when applied on skin, ii) it should bring high doses of humectant and emollient, iii) it should offer a controlled release of incorporated active ingredients iv) it should offer a large capacity for the incorporation of active ingredient(s) and v) it should protect these active ingredients against oxidation. It should also be compatible with standard ways to provide moisturization by non specific skin protection, e.g. with Vaseline, silicones and other common occlusive agents.

In another embodiment of the invention, such formulations are used to deliver molecules of pharmaceutical value through skin or inside the body, for example, through internal application.

Some approaches to optimize the release of molecules of interest after topical applications exist. They are typically based on carriers such as nanocarriers (liposomes, nanocapsules . . . ), which carry the molecules of interest through the skin. However, these approaches lead to internalization of intact carriers, together with all the surfacting molecules used to stabilize them, which in turn leads to high risks of undesired side effects in the short or even long terms (Vega-Villa K. R., et al., Advanced Drug Delivery Reviews 60 (2008) 929-938).

WO 02/24152 describes compositions in the form of an oil-in-glycerin emulsion with mean droplet size below one micron and at least one bioactive compound comprising a hydrophobic moiety within its structure to facilitate stratum corneum and dermal penetrations of the bioactive compound.

U.S. Pat. No. 7,932,294 describes a prodrug containing a chemical link cleavable by enzymes naturally occurring in human physiology, to allow bio availability of the drug under its active form. The active form of the compound was made inactive by grafting a chemical tail that needs to be cleaved by enzymatic systems. However, this approach enables the controlled release of only one compound at a time. It requires to modifying drugs by chemical engineering and subsequent processes of purification. Moreover, the toxicity of the new compound formed, i.e. the prodrug, has to be evaluated.

In addition, it has been reported that molecules of interest could be released as a function of time, temperature, or even electricity (Burrows et al, International Journal of Pharmaceutics, 1994, 111, pp 283-293, Makai et al., International Journal of Pharmaceutics, 2003, 256, pp 95-107; Fong et al, Journal of Controlled Release, 2009, 135, pp 218-226, WO2007113711A2).

However, these approaches suffered from several drawbacks and limitations:

(i) controlled release through temperature changes or through electrical stimulation requires additional devices and are not a practical solution for consumers and patients.

(ii) controlled release over time can be an attractive proposition only if the intact emulsion is in place long enough for slow diffusion of the molecules of interest through the structure. Of note, diffusion through the structure can only occur for hydrophilic molecules, as hydrophobic ones are stably trapped into the oily phase of the lamellar structures.

In real life however, such emulsions are used in two ways:

A) either they are applied topically and rubbed onto skin until the user has the feeling that it has penetrated into the epidermis B) or they are applied onto skin or another (internal) organ and left with a certain width (eg 0.5-10 mm) in contact with skin or any internal organ.

In situation A), rubbing onto skin leads to destruction of the emulsion freeing up immediately the polar and the oily phases and leaving only lamellar structures onto skin (eg Zhang, W. and L. Liu, Journal of Cosmetics, Dermatological Sciences and Applications, 2013, 3, pp 139-144). These lamellar structures, together with any molecules of interest that they may contain, stay on skin until they are washed away or non specifically destroyed (together with any molecule of interest that they may contain) by natural physiology or bacterial mechanisms.

In situation B), the emulsion stays stably in place until it is physically removed, but does not provide the moisturizing effect it is expected to provide as the humectant and emollient agents are trapped into the structure. Only hydrophilic molecules of interest are released, by diffusion through the structure while hydrophobic molecules stay trapped in the oily phase and lamellar structures.

Despite their potential, there are therefore major limitations that prevent the use of these kinds of emulsions for combined moisturizing and controlled release of molecules of interest.

The applicant surprisingly discovered that liquid crystals emulsion can be functionalized so that they are specifically degraded by enzymes expressed by stressed or damaged tissues or bacteria present at the surface of the organ, which constitute the subject of the invention.

The compositions of the invention, being biodegradable, are able to provide both controlled release of ingredients of interest, be they hydrophilic or hydrophobic, as well as preferential moisturizing of damaged, stressed or infected biological surfaces. The use of functionalized liquid crystals emulsions of the invention allows addressing the limitations highlighted above:

in situation A), the lamellar structures that stay on skin are selectively and progressively enzymatically degraded when in contact with inflamed or damaged biological tissue, thereby releasing the molecule of interest they contain at a rate that reflects the tissue needs in situation B), the liquid crystal emulsion in contact with skin is progressively destructed by specific enzymes at the surface of the skin, releasing progressively humectant, emollient and any molecule of interest trapped in the different reservoirs of the structure and thereby providing controlled release of all the compounds contained in the liquid crystals emulsion.

A subject of the invention is therefore a cosmetic method for treating the skin.

Another subject of the invention is a pharmaceutical method for treating an internal tissue, organ or skin subject to disorders.

Other subjects will emerge from reading of the description, the examples and the figures which follow.

Figure 2:
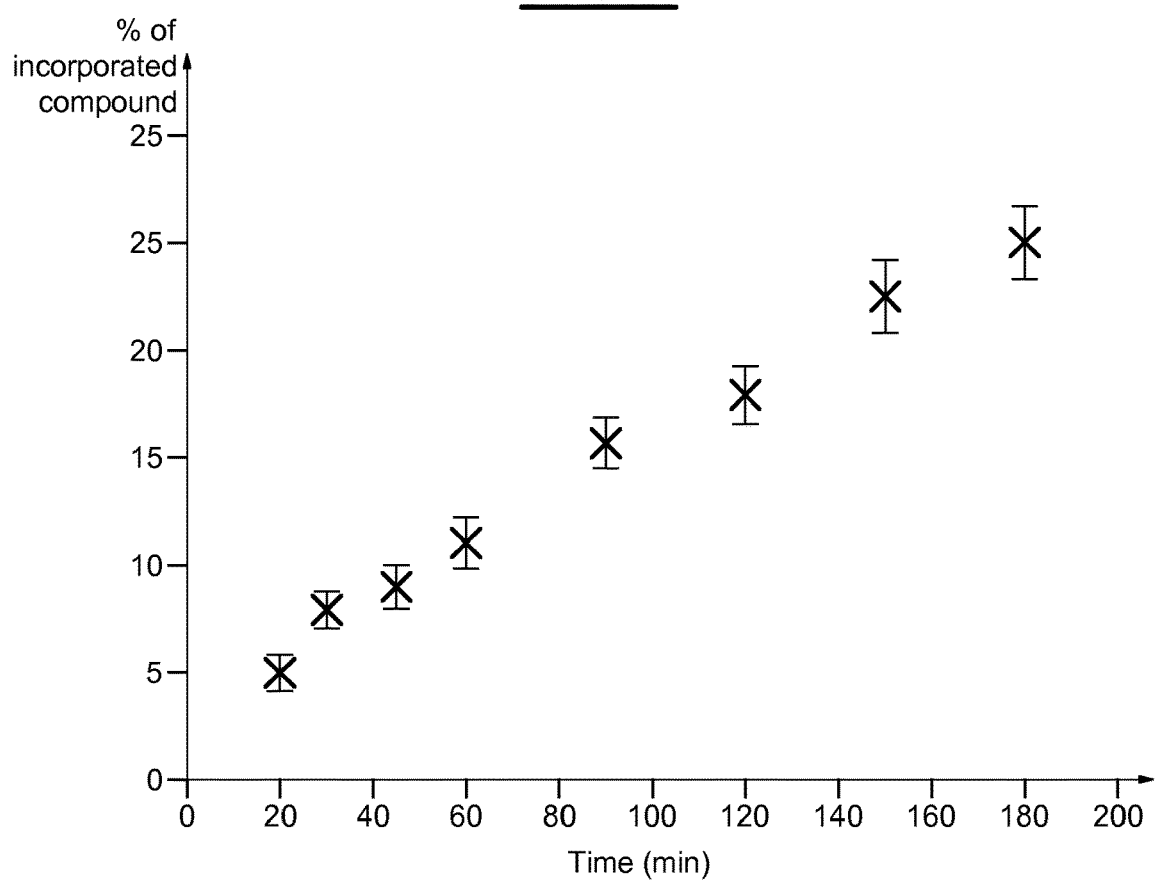
Figure 3:
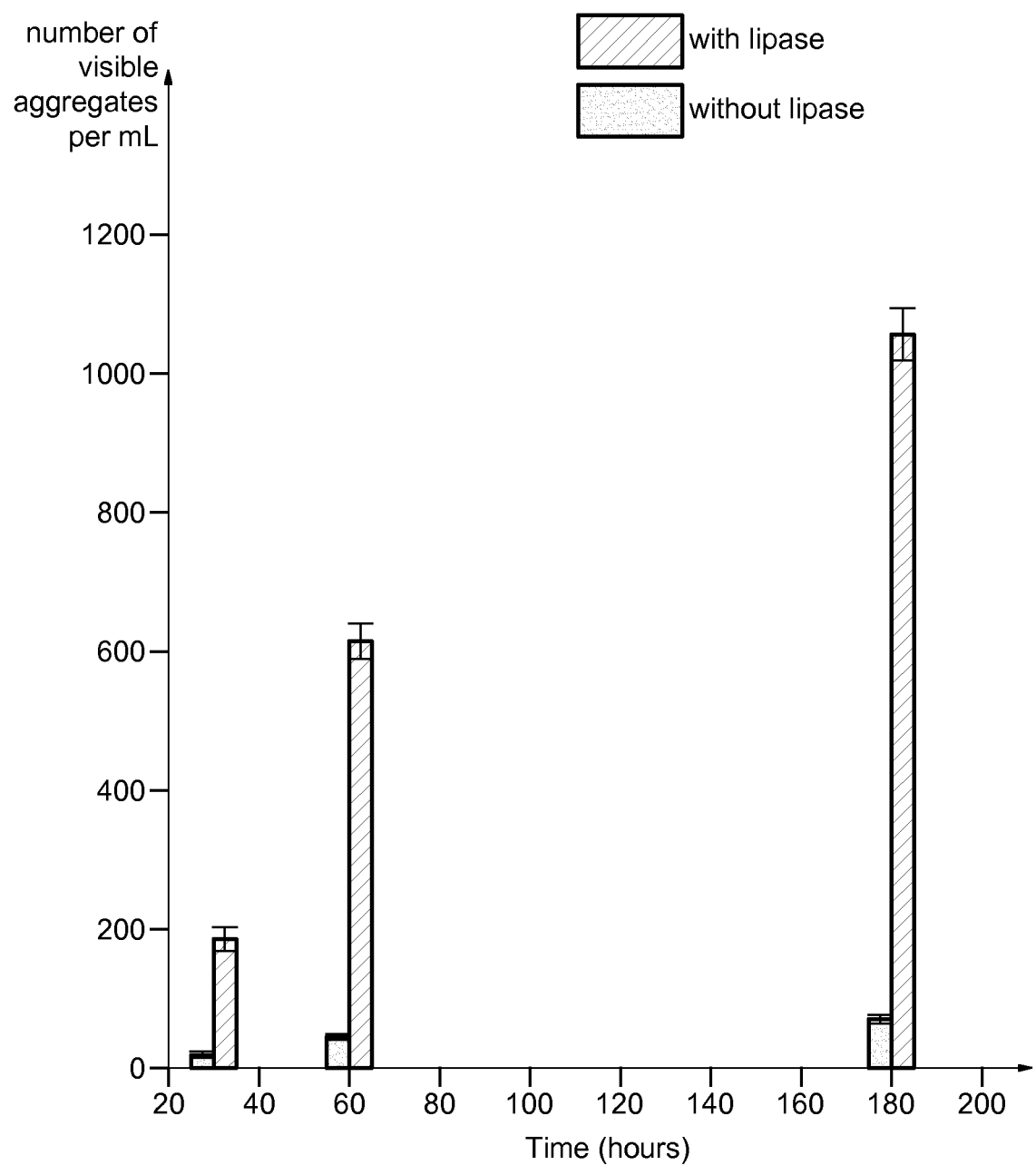

FIG. 1: hydration level measures over a period of 12 days for an untreated area of a human leg skin, and an equivalent area onto which the composition was applied once per day, FIG. 2: percentage of release of a hydrophilic probe incorporated in composition C as a function of time, FIG. 3: number of visible aggregates per mL over time for a composition D immersed either in a 9 g/L NaCl solution (without lipase) or in a 9 g/L NaCl solution with the lipase Lipolase 100L (Sigma Aldrich) (with lipase).

The composition in accordance with the invention comprises, in a cosmetically or pharmaceutical acceptable medium, at least one emulsifier having a cleavable bound, at least one emollient, at least one polar solvent, and water, forming together a macroscopically homogenous liquid crystals emulsion.

The composition is designed to be able to also contain active ingredients that are released over time or depending on external stimulus. The composition is biodegradable and allows the controlled release of pharmaceutical or cosmetic activities including moisturizing activities, soothing activities and therapeutic activities.

In an embodiment, the composition in accordance with the invention comprises, in a cosmetically or pharmaceutically acceptable medium, at least one emulsifier having a bound cleavable, at least one emollient, at least one polar solvent, at least one active ingredient expected to have a cosmetic or pharmaceutical action, and water, forming together a macroscopically homogenous liquid crystals emulsion.

Preferably, the liquid crystals emulsion is formed by at least one emulsifier having an enzyme cleavable bound which is cleavable by an esterase, a metalloproteinase, a lipase or other enzymes expressed by damaged or stressed biological tissue.

In one embodiment of the invention, at least one of the ingredients of the composition is electrically charged, negatively or positively.

Within the meaning of the present invention, the terms "at least one" means one or more and thus includes single compounds as well as mixtures.

Liquid crystals emulsions exhibit properties of both liquid and solid states. Liquid crystals are anisotropic materials that show at least orientational long range order and may show short range order. Liquid crystal phases represent intermediate states and are called mesophases. Such structures are prepared using amphiphilic molecules that are able to self assemble in thermodynamically stable structures that are composed of discrete non polar and polar domains.

Preferably, the emulsifier having an enzyme cleavable bound is glyceryl monoalkanoate, polyglyceryl monoalkanoate, sorbitan monoalkanoate or ascorbyl monoalkanoate.

More preferably, the emulsifier is glyceryl monoalkanoate, polyglyceryl monoalkanoate or ascorbyl monoalkanoate.

Even more preferred, the emulsifier is glyceryl monoalkanoate.

Moreover, several emulsifiers from these lists may be used together.

In the compositions of the invention, the emulsifier is present at an amount comprised between 5 and 40% by weight, preferably by 7% to 30% by weight based on the total weight of the composition.

In the composition according to the invention, the emollient can be:

a) hydrocarbon based plant oil with a high triglyceride content consisting of fatty acid ester of glycerol. The fatty acid may have various chains lengths, and these chains can also be linear or branched and saturated or unsaturated. This plant oil can be avocado oil, apricot kernel oil, blackcurrant seed oil, borage seed oil, camelina seed oil, castor oil, chaulmoogra oil, corn oil, cottonseed oil, cucumber seed oil, grape seed oil, hemp seed oil, *Inca* inchi oil, karite butter, jojoba oil, millet oil, musk rose oil, olive oil, passion flower oil, *perilla* seed oil, rapeseed oil, sunflower oil, sweet almond oil, wheat germ oil.

b) synthetic oils or ester of formula R1COOR2 with R1 and R2 representing a linear or a branched fatty acid residues comprising 4 to 60 carbons. It can be Behenyl Beeswax, Behenyl Behenate, Behenyl Erucate, Behenyl Isostearate Behenyl Olivate, Behenyl/Isostearyl Beeswax, Butyl Avocadate, Butyl Babassuate, Butyl Isostearate, Butyl Myristate, Butyl Oleate, Butyl Stearate, Butyloctyl Beeswax, Butyloctyl Behenate, Butyloctyl Candelillate, Butyloctyl Cetearate, Butyloctyl Oleate, Butyloctyl Palmitate, C10-40 Isoalkyl Acid Octyldodecanol Esters, C14-30 Alkyl Beeswax, C16-36 Alkyl Stearate, C18-38 Alkyl Beeswax, C18-38 Alkyl C24-54 Acid Ester, C20-40 Alkyl Behenate, C20-40 Alkyl Stearate, C30-50 Alkyl Beeswax, C30-50 Alkyl Stearate, C32-36 Isoalkyl Stearate, C40-60 Alkyl Stearate, C4-5 Isoalkyl Cocoate, Caprylyl Butyrate, Caprylyl Caprylate Caprylyl Eicosenoate Cetearyl Behenate Cetearyl Candelillate Cetearyl Isononanoate Cetearyl Nonanoate, Cetearyl Olivate, Cetearyl Palmate, Cetearyl Palmitate, Cetearyl Rice Branate, Cetearyl Stearate, Cetyl Babassuate, Cetyl Behenate, Cetyl Caprate, Cetyl Caprylate, Cetyl Dimethyloctanoate, Cetyl Esters, Cetyl Isononanoate, Cetyl Laurate, Cetyl Myristate, Cetyl Myristoleate, Cetyl Oleate, Cetyl Palmitate, Cetyl Ricinoleate, Cetyl Stearate, Cetyl Tallowate, Chimyl Isostearate, Chimyl Stearate, Coco-Caprylate, Coco-Caprylate/Caprate Coco-Rapeseedate, Decyl Castorate, Decyl Cocoate, Decyl Isostearate, Decyl Jojobate, Decyl Laurate, Decyl Myristate, Decyl Oleate, Decyl Olivate, Decyl Palmitate, Decyltetradecyl Cetearate, Erucyl Arachidate, Erucyl Erucate, Erucyl Oleate, Ethylhexyl Adipate/Palmitate/Stearate, Ethylhexyl C10-40 Isoalkyl Acidate, Ethylhexyl Cocoate, Ethylhexyl Hydroxystearate, Ethylhexyl Isononanoate, Ethylhexyl Isopalmitate, Ethylhexyl Isostearate, Ethylhexyl Laurate, Ethylhexyl Myristate, Ethylhexyl Neopentanoate, Ethylhexyl Oleate, Ethylhexyl Olivate, Ethylhexyl Palmitate, Ethylhexyl Pelargonate, Ethylhexyl Stearate, Heptyl Undecylenate, Heptylundecyl Hydroxystearate, Hexyl Isostearate, Hexyl Laurate, Hexyldecyl Hexyldecanoate, Hexyldecyl Isostearate, Hexyldecyl Laurate, Hexyldecyl Oleate, Hexyldecyl Palmitate, Hexyldecyl Stearate, Hexyldodecyl/Octyldecyl Hydroxystearate, Hydrogenated Castor Oil Behenyl Esters, Hydrogenated Castor Oil Cetyl Esters, Hydrogenated Castor Oil Stearyl Esters, Hydrogenated Ethylhexyl Olivate, Hydrogenated Ethylhexyl Sesamate, Hydrogenated Isocetyl Olivate, Hydrogenated Isopropyl Jojobate, Hydroxycetyl Isostearate, Hydroxyoctacosanyl Hydroxystearate, Isoamyl Laurate, Isobutyl Myristate, Isobutyl Palmitate, Isobutyl Perlargonate, Isobutyl Stearate, Isobutyl Tallowate, Isocetyl Behenate, Isocetyl Isodecanoate, Isocetyl Isostearate, Isocetyl Laurate, Isocetyl Myristate, Isocetyl Palmitate, Isocetyl Stearate, Isodecyl Cocoate, Isodecyl Hydroxystearate, Isodecyl Isononanoate, Isodecyl Laurate, Isodecyl Myristate, Isodecyl Neopentanoate, Isodecyl Oleate, Isodecyl Palmitate, Isodecyl Stearate, Isohexyl Caprate, Isohexyl Laurate, Isohexyl Neopentanoate, Isohexyl Palmitate, Isolauryl Behenate, Isononyl Isononanoate, Isooctyl Caprylate/Caprate, Isooctyl Tallate, Isopropyl Arachidate, Isopropyl Avocadate, Isopropyl Babassuate, Isopropyl Behenate, Isopropyl Hydroxystearate, Isopropyl Isostearate, Isopropyl Jojobate, Isopropyl Laurate, Isopropyl Linoleate, Isopropyl Myristate, Isopropyl Oleate, Isopropyl Palmitate, Isopropyl Ricinoleate, Isopropyl Stearate, Isopropyl Tallowate, Isostearyl Avocadate, Isostearyl Behenate, Isostearyl Erucate, Isostearyl Hydroxystearate, Isostearyl Isononanoate, Isostearyl Isostearate, Isostearyl Laurate, Isostearyl Linoleate, Isostearyl Myristate, Isostearyl Neopentanoate, Isostearyl Palmitate, Isotridecyl Isononanoate, Isotridecyl Laurate, Isotridecyl Myristate, Isotridecyl Stearate, Lauryl Behenate, Lauryl Cocoate, Lauryl Isostearate, Lauryl Laurate, Lauryl Myristate, Lauryl Oleate, Lauryl Palmitate, Lauryl Stearate, Lignoceryl Erucate, Myristyl Isostearate, Myristyl Laurate, Myristyl Myristate, Myristyl Neopentanoate, Myristyl Stearate, Octyldecyl Oleate, Octyldodecyl Avocadoate, Octyldodecyl Beeswax, Octyldodecyl Behenate, Octyldodecyl Cocoate, Octyldodecyl Erucate, Octyldodecyl Hydroxystearate, Octyldo decyl Isostearate, Octyldodecyl Meadowfoamate, Octyldodecyl Myristate, Octyldodecyl Neodecanoate, Octyldodecyl Neopentanoate, Octyldodecyl Octyldodecanoate, Octyldodecyl Oleate, Octyldodecyl Olivate, Octyldodecyl Ricinoleate, Octyldodecyl Safflowerate, Octyldodecyl Stearate, Oleyl Arachidate, Oleyl Erucate, Oleyl Linoleate, Oleyl Myristate, Oleyl Oleate, Oleyl Stearate, Propylheptyl Caprylate, Stearyl Beeswax, Stearyl Behenate, Stearyl Caprylate, Stearyl Erucate, Stearyl Heptanoate, Stearyl Linoleate, Stearyl Olivate, Stearyl Palmitate, Stearyl Stearate, Tetradecyleicosyl Stearate, Tetradecyloctadecyl Behenate, Tetradecyloctadecyl Hexyldecanoate, Tetradecyloctadecyl Myristate, Tetradecyloctadecyl Stearate, Tetradecylpropionates, Tridecyl Behenate, Tridecyl Cocoate, Tridecyl Erucate, Tridecyl Isononanoate, Tridecyl Laurate, Tridecyl Myristate, Tridecyl Neopentanoate, Tridecyl Stearate.

Preferably, the emollient is hydrocarbon-based plant oil. Among them, *Ricinus communis* seed oil, canola oil, apricot kernel oil, grape seed oil, cucumber oil, blackcurrant seed oil are more preferred.

The emollient is present at an amount comprised from 3% to 60%, preferably from 10% to 30% by weight, based on the total weight of the composition.

The polar solvent can be glycerol, water dimethylsulfoxyde, ethylene glycol, acetone, ethanol and any combination thereof.

In the compositions of the invention, a preferred polar solvent is glycerol.

The polar solvent is present in the compositions according to the invention in an amount comprised from 5% to 60%, preferably from 10% to 30% by weight, based on the total weight of the composition.

Water is present in the composition in an amount of 10 to 70% by weight, preferably from 20% to 50%, based on the total weight of the composition.

When the at least one active ingredient is present in the compositions of the invention, this active ingredient is present in an amount of from 0.1% to 20% by weight, based on the total weight of the composition.

Preferably, the at least one active ingredient is a hydrophilic or hydrophobic compound.

More preferably, in the composition of the invention, the at least one active ingredient that can be added is:

allantoin, aloe vera, bisabolol, alphahydroxyacid (AHA), beta sitosterol, ubiquinone, curcumin and its derivatives, glycyrrhetinic acid, its salts and its derivates, alpha-lipoic acid, essential oils such as clove oil, plant extracts such as palm oil extracts, beta-glucan oat, boswelic acid, *Ginko biloba* extract, green tea leaf extract, *Eleis guineensis* leaf extract, *Chelidonium*, Silymarin, soy isoflavones, Pomegranate, phytosterols, menthol, quercetin, resveratrol, fucoidan, betahydroxyacid (BHA), hyaluronic acid, urea, vitamin E and its derivates, vitamin C and its derivates, vitamins B, niacinamide, and its derivates, vitamine K and any combination thereof, Ingenol mebutate, steroids, non-steroidal anti-inflammatory drugs (such as Ibuprofen, Ketoprofen, Indometacin, Piroxicam), corticosteroids, retinoids (such as tarazotene, tretinoin and isotretinoin), vitamin D and its derivatives (such as calcipotriol), vismodegib, doxorubicin, paclitaxel, salicylic acid and its derivates, dithranol (or anthraline), immune-modulating agents such as tacrolimus, fluorouracyl, pimecrolimus, imiquimod, interferons, glatiramer acetate, natalizumab, calcineurin inhibitors, TNF-alpha, cytotoxic and immunosuppressing agents such as methotrexate, mycophenolate mofetil, 6-thioguanine, aziatoprine, monocyclosporine A, sirolimus, mycophenolic acid and its derivates, antibiotics or anti bacterial molecules such as sulfonamide, mafenide acetate, silver sulfadiazine, silver salts, mupirocin, metronidazole, erythromycine, clindamycin, metronidazole, bacitracin, polymixin B, neomycin, antifungal agents such as itraconazole, terbinafine, ciclopirox, clotrimazole, econazole, ketoconazole, miconazol, naftifine, oxiconazole, terbinafine, tolnaftate, drugs for cutaneous viral infections such as podophyllotoxin, agents to treat acne condition such as benzoyl peroxide, antihistaminic agent such as doxepin, anesthetics molecules, such as benzocaine, tetracaine, lidocaine, procaine, opioids such as morphine, codeine, thebaine, oxycodone, tramadol, methadone.

Even more preferably, the at least one active ingredient is chosen among allantoin, bisabolol, glycyrrhetinic acid, menthol, niacinamide and dithranol.

The composition of the invention is used as a vehicle for mixed or sustained delivery of active cosmetic or pharmaceutical ingredients to the skin.

The term "mixed delivery" of an active ingredient is defined for purposes of the present invention as the release of an active ingredient during application due to partial deconstruction of the gel structure while applying the composition. Indeed, when a composition of the present invention is spread and strongly rubbed onto skin, the polar and oil compartments containing the said active ingredient are 'immediately delivered' to the skin, whereas the active ingredients contained in the microstructures forming the third compartment, which remains on skin, are released sustainably as the structure is degraded specifically by enzyme.

The term "sustained delivery" is defined for purposes of the present invention as a method of active ingredient delivery where the rate of release of the active ingredient from the formulation is not solely dependent on the concentration of active ingredient remaining in the formulation and/or the solubility of the active ingredient in the medium surrounding the formulation. For a composition coated on skin without rubbing, the structure of the gel remains intact and sustained delivery is occurring on the whole structure, i.e. for all the ingredients contained in the three compartments: oil compartments, polar compartment and the microstructures formed by the organization of emulsifiers in liquid crystal network. The release of the active ingredients results of the degradation of the gel by enzyme cleaving the ester bond of the emulsifier, inducing the disorganization of the microstructures that hold the macrostructure together.

By "topical administration", as used herein, is meant directly laying or spreading upon epidermal tissue, especially outer skin or membrane, including the skin or membrane of the oral or vaginal cavities or eyes.

In an embodiment of the present invention, the composition of the present invention may include one or more additional components. Such additional components include but are not limited to anti-perspirants, anti-static agents, buffering agents, bulking agents, chelating agents, cleansers, colorants, conditioners, deodorants, diluents, dyes, fragrances, humectants, pearlescent aids, perfuming agents, permeation enhancers, pH-adjusting agents, preservatives, protectants, skin penetration enhancers, solubilizers, sunscreens, sun blocking agents, sunless tanning agents, viscosity modifiers and vitamins. As is known to one skilled in the art, in some instances, a specific additional component may have more than one activity, function or effect.

A person skilled in the art will take care to choose these optional additives and their amounts so that they do not harm the properties of the compositions of the present invention.

The composition of the invention may be used as a skin moisturizer, a skin protectant, or a skin smoother.

The compositions of the invention may be used to cosmetically and topically treat the skin.

The composition of the invention may also be used as a medicament, in particular, for its use to prevent or treat dermatological skin disorders. The compositions of the invention can indeed deliver, through topical application, drugs that are recommended for treatment of various skin conditions like psoriasis, eczema, wounds, burns, keloid, atopic dermatitis, ichthyosis, precancerous carcinoma, basal-cell carcinoma, acne, lupus, rosacea, Urticaria, wart, cutaneous candidiasis, cellulitis, actinic keratosis, stasis dermatitis and ulcers, Netherton syndrome, old age melanoma, xeroderma, Paget's disease, painful diabetic neuropathy, scabies and lices, pruritus, Kaposi's sarcoma.

External topical administration is an important route for the administration of drugs in disease treatment, like for example, antibiotic, anti-fungal, anti-inflammatory, anesthetic, analgesic, anti-allergic, corticosteroid, retinoid and anti-proliferative medications.

The advantages of this form of delivery include, but are not limited to: avoidance of the risks associated with parenteral treatment; elimination of the inconveniences of parenteral treatment; avoidance of the variable rates of absorption and metabolism inherent in oral treatment; increasing the continuity of drug administration by permitting delivery of agents with short biological half-lives; and elimination of gastrointestinal irritation resulting from exposing the gastrointestinal tract to pharmaceutically active ingredient, preservatives, tableting agents, and the like. Most importantly, topical delivery possesses the potential for effectively treating conditions which are local in nature (or which exhibit local manifestations), systemically as well as locally with the same treatment regimen.

The compositions of the invention can also be used or to treat mucous membrane such as bucal mucosa, bronchial mucosa, endometrium, gastric mucosa, intestinal mucosa, nasal mucosa or in internal medicine like for knee cavities, eyes, eardrums, hair, skull, or organs accessible through the abdominal cavity.

Its administration can be done through a variety of methods including endoscopy, coelioscopy, enema, intravitreal administration or mesotherapy. It can be applied by administering the composition as a treatment it itself, or after a surgery has been performed, to help restoring healthy condition of the treated area, by example by local delivery anti-inflammatory, anti-infectious or anti-cancerous drugs on the lesioned area.

Accordingly, the compositions of the invention are useful to treat diseases like sarcoidosis, arthritis, osteitis, osteoarthritis, osteomyelitis, vesiculitis, inflammatory bowel disease, Pelvic inflammatory diseases, uveitis, gastritis, glioblastoma, retinoblastoma, myocarditis, mucositis, mucitis, diabetes, urethritis, bladder infections and inflammation, bacterial and fungal infections of the intestinal or gastrointestinal track or of the sexual organs, graft versus host disease (GvHD), post graft treatments, acute and chronic pain of skin or internal organs.

Alternatively, the compositions of the invention are useful to treat diabetic ulcer, foot and mouth disease, post surgery and post cancer treatment (eg breast cancer)

Compositions of the present invention can as well been used as skin supportive care to help patient recovering from treatments with severe secondary effects such as radiotherapy and chemotherapy, that can induce severe dehydration of skin and mucosa.

The compositions of the invention are a vehicle for mixed or sustained delivery of active pharmaceutical ingredient to the skin, mucosa or internal organs.

A pharmaceutical or cosmetic composition of the present invention is very easy to use. When applied onto the afflicted body surface of mammals, i.e., humans or animals, it freely spreads on the surface and gives a comfortable feel.

In addition, compositions of the invention may also be further functionalized by using electrically charged or otherwise engineered emulsifiers or other ingredients, so that the compositions preferentially attach to inflamed or damaged tissue.

Depending on the method of administration, the compositions according to the invention can be in all the forms usually employed in cosmetics or as medication. Said compositions can in particular be formulated as ointments, creams, milks, gels, sprays, sticks, films and coatings, shampoos, lotions or in capsules.

The present invention relates to a method to deliver through the skin at least one active ingredient and pharmaceutically treat the skin, using the composition of the invention.

The present invention is also relative to a method to internally deliver at least one active ingredient by using a composition of the invention and particularly, to target and deliver active ingredients of interest to inflamed tissue like internal organs, mucosa or membranes, using such a composition.

The present invention concerns also a method to protect against oxidation an active ingredient by using a composition of the invention. Indeed, the compound of interest is entrapped in a matrix that helps to protect it from oxidation, that hence increases the chemical stability of the compound.

The invention is described with reference to the following examples. This invention is not limited to these examples and experiments. Many variations will suggest themselves and are within the full intended scope of the appended claims.

EXAMPLE 1: PREPARATION OF A MOISTURIZING LIQUID CRYSTALS Emulsion

A liquid crystals emulsion, whose composition is described in Table 1 below, is prepared according to the following protocol:

| Ingredients | % of total weight |
| --- | --- |
| Glycerin | 15 |
| Sorbitan stearate | 8 |
| castor oil | 10 |
| Water | qs 100 |

Briefly, sorbitan stearate and glycerin are mixed under stirring at 75° C. Then, castor oil is added, and the mixture is stirred at 75° C. for 15 minutes. Water is added in the mixture and the composition is let to cool down at room temperature.

EXAMPLE 2: MOISTURIZING PROPERTIES OF THE COMPOSITION AFTER 1 Hour

To evaluate the moisturizing properties of a composition of the invention, experiments have been conducted by measuring its moisturizing properties on skin.

The hydration measures were made using a capacitance skin moisture sensor (MoistSense, Monaderm). This sensor measures the change in the dielectric constant due to skin surface hydration. The measurement can detect even slight changes in the hydration level and results are expressed as percentage of hydration.

A composition A made of ascorbyl palmitate 8%, glycerol 25%, castor oil 15%, bisabolol 1%, water qs 100% by weight and whose pH was stabilized at 5 using saturated solution of calcium hydroxide, is prepared according to the protocol of example 1.

To estimate the hydrating properties of the liquid crystals gel network composition A, hydration measures were recorded before the application of the composition, and 1 hour after application on 8 volunteers.

Mean of 10 measures for each points at t=0 and after 1 h were used to evaluate the increase in skin hydration. The percentages are expressed in % of hydration increase on skin with the composition A, compared with skin without gel. They are reported in Table 2 below.

| Subject n° | % hydration increase after 1 hour |
| --- | --- |
| 1 | +25% (+/−2.5%) |
| 2 | +20% (+/−2%) |
| 3 | +46% (+/−5%) |
| 4 | +37% (+/−4%) |
| 5 | +19% (+/−2%) |
| 6 | +54% (+/−5%) |
| 7 | +32% (+/−3%) |
| 8 | +62% (+/−6%) |

For all the volunteers tested, the hydration level was higher 1 hour after application of the composition.

The results show that this composition, under the form of liquid crystals gel network, is efficient to increase skin hydration after 1 hour.

EXAMPLE 3: MOISTURIZING PROPERTIES OF THE COMPOSITION OVER A Long Period of Time A human volunteer has tested for 12 days the moisture provided by the composition B containing glycerin 22%; glyceryl monostearate 9%, castor oil 13%, beeswax 1%, a liquid blend of pentylene glycol, caprylyl glycol and decylene glycol sold under the trademark microcare emollient DCP (Thor Care) 1%, H2O 54%. Each day, the volunteer recorded her hydration level using a MoistSense hydration skin sensor (Monaderm) after taking a shower and before applying composition. A baseline was recorded by measuring hydration level on a skin area equivalent to the tested area, but without any hydrating product applied on it during the 12 days of the test. The tested areas were lower leg skin. Each data is the mean of at least 6 measures and results are displayed in FIG. 1, which indicates the measures recorded over the test period for the treated area and the untreated area.

As seen on FIG. 1, the hydrating level is always higher on the area treated with composition B, compared to an untreated similar area.

Indeed, the use of the composition B on skin significantly increases the level of hydration during at least 24 hours. Moreover, its efficiency does not decrease with the use of the product over a long period of time.

EXAMPLE 4: RELEASE OF AN HYDROPHILIC PROBE

A composition C with a gel liquid network structure and of formula glycerin 25%, glyceryl stearate 15%, castor oil 15%, water containing black ink (Waterman) qs 100% has been tested to determine the kinetics of release of hydrophilic compounds.

Briefly, 2.5 g of composition C was immersed in a beaker containing 2.5 mL of NaCl solution at 9 g/L. The amount of released hydrophilic probe (black ink) in the bulk was estimated using colorimetric standard solutions corresponding to the amount of black ink contained in the immersed sample. Results are shown in FIG. 2.

As it can be seen on this FIG. 2, a bell-shaped profile at short time, characteristic of a burst release of a probe, is not observed. On the contrary, the release of the hydrophilic probe is regular in time, as a consequence of the gel liquid crystals network structure of the composition C.

EXAMPLE 5: ACTIVATED DEGRADATION OF THE GEL BY AN ESTERASE

To evaluate the degradation of the composition in an physiological environment, a composition D (25% glycerine, 15% glyceryl stearate, 15% castor oil, 45% H2O) has been immersed either in a 9 g/L NaCl solution, or in a 9 g/L NaCl solution containing an esterase, Lipolase 100L (Sigma Aldrich), at 2500 U/g, to mimic inflammatory processes.

To evaluate the degradation of the sample, numbers of visible aggregates in the solution were counted over time. The higher this number is, the higher the degradation of the composition is effective. The results are reported in FIG. 3.

As it is clearly seen in FIG. 3, the kinetic of degradation is drastically different depending on the presence of the esterase. Using an emulsifier having an enzyme cleavable bound enables to adapt the kinetics of degradation of the liquid crystals composition, and thus kinetics of release of ingredients incorporated in the core of the structure. Indeed, the structure of this specific composition clearly provides controlled release of both moisturizing and cosmetic ingredients.

EXAMPLE 6: PROTECTIVE PROPERTIES TOWARD OXIDATION

To test the protective properties of a composition against oxidation, 0.1% of dithranol, a drug used for psoriasis treatment and very sensitive to oxidation, has been incorporated in a composition E according to the invention, comprising glyceryl stearate 25%, glycerol 25%, castor oil 15%, and water qsp 100%, based of total weight of the composition. A mixture containing the same ingredients but not under the form of liquid crystals composition has been tested as a control experiment (composition F).

The compositions were allowed to rest under daylight at room temperature for 1 month, and the oxidation of dithranol was estimated by the appearance of brown color.

For the composition E (in a liquid gel network), the dithranol started to turn brownish at the interface air/composition after 3 to 5 days. After these first layers were oxidized, the proportion of brown turning composition remained stable for at least 1 month.

For the composition F, the dithranol in the composition started to turn brown after 3 days. Moreover, the change in color appeared in the overall composition and not only in the upper layer in direct contact with air.

These results show that incorporating dithranol in a liquid crystals gel network has enabled to protect the compound toward oxidation.

EXAMPLE 7: A TOPICAL COMPOSITION WITH DITHRANOL

A composition comprising glycerol 25%; castor oil 15%; glyceryl stearate 30%, dithranol 0.5%, water qs 100% is prepared according to the following procedure. Glyceryl stearate and glycerol are heated at 70° C. until melting of glyceryl stearate. Then, castor oil containing dithranol is added under stirring. Water is then added to the mixture and the composition is let to cool down.

The composition can be applied on the psoriatic area once a day at a concentration of 4 mg/cm$^2$ of skin.

The invention claimed is:

1. A topical composition consisting of, in a cosmetically acceptable medium, a liquid crystals emulsion, said composition consisting of:
   a) from 7% to 30% by weight, based on the total weight of the composition, of at least one type of emulsifier having a bond cleavable by an enzyme, wherein the emulsifier is glyceryl monoalkanoate, ascorbyl alkanoate, sorbitan monoalkanoate;
   b) from 10% to 30% by weight, based on the total weight of the composition, of at least one emollient, which is a hydrocarbon based plant oil,
   c) from 10% to 30% by weight, based on the total weight of the composition, of a single polar solvent, which is glycerol, and
   d) 20% to 70% by weight water.

2. A topical composition consisting of, in a cosmetically acceptable medium, a liquid crystals gel network, said composition consisting of:
   a) from 7% to 30% by weight, based on the total weight of the composition, of at least one type of emulsifier having an enzyme cleavable bond, wherein the emulsifier is glyceryl monoalkanoate, polyglyceryl monoalkanoate, sorbitan monoalkanoate;
   b) from 10% to 30% by weight, based on the total weight of the composition, of at least one emollient, which is a hydrocarbon based plant oil,
   c) from 10% to 30% by weight, based on the total weight of the composition, of at least one polar solvent, which is glycerol,
   d) at least one active ingredient, selected from the group consisting of allantoin, bisabolol, beta sitosterol, ubiquinone, curcumin, glycyrrhetinic acid, and its salts, alpha-lipoic acid, clove oil, palm oil extracts, beta-glucan oat, boswelic acid, gingko biloba extract, green tea leaf extract, *Eleis guineensis* leaf extract, *Chelidonium*, silymarin, soy isoflavones, pomegranate, phytosterols, menthol, quercetin, resveratrol, fucoidan, urea, and any combination thereof, and
   e) 20% to 70% by weight water.

3. The composition of claim 1, wherein the emulsifier having an enzyme cleavable bond is cleavable by an esterase, a metalloproteinase or a lipase.

4. The composition of claim 2, wherein the at least one active ingredient is present from 0.1% to 20% by weight, based on the total weight of the composition.

5. The composition of claim 2, which is a vehicle for mixed or sustained delivery of said at least one active ingredient to the skin.

6. A method of cosmetically treating the skin, membranes and mucosa of oral and vaginal cavities, comprising applying the composition of claim 1.

7. A composition consisting of a liquid crystals gel network, said composition consisting of:
   a) from 7% to 30% by weight, based on the total weight of the composition, of at least one type of emulsifier having an enzyme cleavable bound, wherein the emulsifier is glyceryl monoalkanoate, polyglyceryl monoalkanoate, or sorbitan monoalkanoate;
   b) from 10% to 30% by weight, based on the total weight of the composition, of at least one emollient, which is a hydrocarbon based plant oil,
   c) from 10% to 30% by weight, based on the total weight of the composition, of at least one polar solvent, which is glycerol, d) at least one active ingredient, selected from the group consisting of ingenol mebutate, steroids, non-steroidal anti-inflammatory drugs, corticosteroids, retinoids, vitamin D, vismodegib, doxorubicin, paclitaxel, salicylic acid, tacrolimus, fluorouracyl, pimecrolimus, imiquimod, interferons, glatiramer acetate, natalizumab, calcineurin inhibitors, TNF-alpha, methotrexate, mycophenolate mofetil, 6-thioguanine, aziatoprine, monocyclosporine A, sirolimus, mycophenolic acid, dithranol, sulfonamide, mafenide acetate, silver sulfadiazine, silver salts, mupirocin, metronidazole, erythromycine, clindamycin, metronidazole, bacitracin, polymixin B, neomycin, itraconazole, terbinafine, ciclopirox, clotrimazole, econazole, ketoconazole, miconazol, naftifine, oxiconazole, terbinafine, tolnaftate, podophyllotoxin, benzoyl peroxide, benzocaine, tetracaine, lidocaine, procaine, opioids and doxepin, and e) 20% to 70% by weight water, as a medicament.

8. The composition of claim 7, wherein the active ingredient is dithranol.

9. A composition according to claim 7, configured for use to treat dermatological skin disorders.

10. A composition according to claim 9, configured for use to treat psoriasis, wounds and ulcers, burns, or ichthyosis.

11. A composition according to claim 7, configured for use to treat sarcoidosis, arthritis, osteitis, osteoarthritis, osteomyelitis, vesiculitis, inflammatory bowel disease, pelvic inflammatory diseases, uveitis, gastritis, glioblastoma, retinoblastoma, myocarditis, mucositis, mucitis, diabetes, urethritis, bladder infections and inflammation, bacterial and fungal infections of the intestinal or gastrointestinal track or of the sexual organs, graft versus host disease (GvHD), post graft treatments, or chronic and acute pain of skin and internal organs.

12. A composition of claim 7, which is a vehicle for mixed or sustained delivery of an active pharmaceutical ingredient to the skin, mucosa, or internal organs.

13. A method of pharmaceutically treating the skin, comprising applying the composition of claim 7.

14. A method of delivering through the skin at least one active ingredient by using a composition of claim 7.

15. A method of internally delivering at least one active ingredient by using a composition of claim 7.

16. A method of targeting and delivering active ingredients of interest to inflamed tissue using a composition of claim 7.

17. A method of stabilizing an active ingredient by using a composition of claim 2.

18. The composition of claim 2, wherein the emulsifier having an enzyme cleavable bond is cleavable by an esterase, a metalloproteinase or a lipase.

19. The composition of claim 7, wherein the emulsifier having an enzyme cleavable bond is cleavable by an esterase, a metalloproteinase or a lipase.

20. The composition of claim 7, wherein the at least one active ingredient is present from 0.1% to 20% by weight, based on the total weight of the composition.

21. A method of stabilizing an active ingredient by using a composition of claim 7.

* * * * *